United States Patent
Patil et al.

(10) Patent No.: US 8,865,959 B2
(45) Date of Patent: Oct. 21, 2014

(54) PROCESS FOR SYNTHETIC LUBRICANT PRODUCTION

(75) Inventors: Abhimanyu Onkar Patil, Westfield, NJ (US); Margaret May-Som Wu, Skillman, NJ (US); Norman Yang, Westfield, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 918 days.

(21) Appl. No.: 12/380,830

(22) Filed: Mar. 4, 2009

(65) Prior Publication Data

US 2009/0240012 A1    Sep. 24, 2009

Related U.S. Application Data

(60) Provisional application No. 61/069,826, filed on Mar. 18, 2008.

(51) Int. Cl.
| | | |
|---|---|---|
| *C07C 2/22* | (2006.01) | |
| *C07C 2/34* | (2006.01) | |
| *C10G 50/02* | (2006.01) | |
| *C08F 210/14* | (2006.01) | |

(52) U.S. Cl.
CPC ... *C07C 2/22* (2013.01); *C07C 2/34* (2013.01); *C10G 50/02* (2013.01); *C07C 2527/126* (2013.01); *C07C 2531/14* (2013.01); *C07C 2531/22* (2013.01); *C08F 210/14* (2013.01); *C10G 2400/10* (2013.01)
USPC ........... 585/517; 585/502; 585/520; 585/521; 585/522; 585/523; 585/525; 585/530; 585/532

(58) Field of Classification Search
USPC ......... 585/500, 502, 517, 520, 521, 525, 530, 585/532, 522, 523
See application file for complete search history.

(56) References Cited

U.S. PATENT DOCUMENTS

| | | | |
|---|---|---|---|
| 2,978,442 A | 4/1961 | Brightbill et al. | |
| 3,149,178 A | 9/1964 | Hamilton et al. | |
| 3,164,578 A | 1/1965 | Baker et al. | |
| 3,382,291 A | 5/1968 | Brennan | |
| 3,742,082 A | 6/1973 | Brennan | |
| 3,769,363 A | 10/1973 | Brennan | |
| 3,780,128 A | 12/1973 | Shubkin | |
| 3,876,720 A | 4/1975 | Heilman et al. | |
| 3,883,417 A | 5/1975 | Woo et al. | |
| 4,016,349 A | 4/1977 | McKenna | |
| 4,132,663 A | 1/1979 | Heilman et al. | |
| 4,149,178 A | 4/1979 | Estes | |
| 4,172,855 A * | 10/1979 | Shubkin et al. ................. 585/16 |
| 4,180,575 A | 12/1979 | Rochling et al. | |
| 4,239,930 A * | 12/1980 | Allphin et al. ................. 585/517 |
| 4,263,465 A | 4/1981 | Sheng et al. | |
| 4,263,712 A | 4/1981 | Schroder | |
| 4,367,352 A | 1/1983 | Watts, Jr. et al. | |
| 4,413,156 A | 11/1983 | Watts, Jr. et al. | |
| 4,434,408 A | 2/1984 | Baba et al. | |
| 4,451,684 A | 5/1984 | Pasky | |
| 4,469,912 A | 9/1984 | Blewett et al. | |
| 4,587,368 A | 5/1986 | Pratt | |
| 4,587,374 A | 5/1986 | Peters | |
| 4,701,489 A | 10/1987 | Hughes et al. | |
| 4,704,491 A | 11/1987 | Tsutsui et al. | |
| 4,827,064 A | 5/1989 | Wu | |
| 4,827,073 A | 5/1989 | Wu | |
| 4,892,851 A | 1/1990 | Ewen et al. | |
| 4,910,355 A | 3/1990 | Shubkin et al. | |
| 4,912,272 A | 3/1990 | Wu | |
| 4,914,254 A | 4/1990 | Pelrine | |
| 4,926,004 A | 5/1990 | Pelrine et al. | |
| 4,950,822 A | 8/1990 | Dileo et al. | |
| 4,956,122 A | 9/1990 | Watts et al. | |
| 4,962,262 A | 10/1990 | Winter et al. | |
| 4,967,032 A | 10/1990 | Ho et al. | |
| 4,990,709 A | 2/1991 | Wu | |
| 4,990,771 A | 2/1991 | Minoura et al. | |
| 5,012,020 A | 4/1991 | Jackson et al. | |
| 5,017,299 A | 5/1991 | Gutierrez et al. | |
| 5,017,714 A | 5/1991 | Welborn, Jr. | |
| 5,068,487 A | 11/1991 | Theriot | |
| 5,087,788 A | 2/1992 | Wu | |
| 5,177,276 A | 1/1993 | Beach et al. | |
| 5,186,851 A | 2/1993 | Gutierrez et al. | |
| 5,188,724 A | 2/1993 | Heilman et al. | |
| 5,220,100 A | 6/1993 | Massie et al. | |
| 5,264,642 A | 11/1993 | Wu | |

(Continued)

FOREIGN PATENT DOCUMENTS

| | | |
|---|---|---|
| EP | 0 277 004 | 8/1988 |
| EP | 0 277 007 | 8/1988 |

(Continued)

OTHER PUBLICATIONS

U.S. Appl. No. 61/008,095, filed Dec. 18, 2007.

(Continued)

*Primary Examiner* — In Suk Bullock
*Assistant Examiner* — Bradley Etherton
(74) *Attorney, Agent, or Firm* — Robert A. Migliorini; Luke A. Parsons

(57) ABSTRACT

A process for the preparation of oligomeric poly alpha-olefins includes oligomerizing low molecular weight PAO oligomer in the presence of a Lewis acid catalyst such as promoted aluminum trichloride or boron trifluoride under oligomerization conditions. The low molecular weight PAO oligomers used as a feed or feed component of the present process are the light olefinic by-product fractions including the dimers and light fractions from the metallocene-catalyzed PAO oligomerization process which are characterized by a molecular weight of 150 to 600 and a terminal olefin (vinylidene) content of at least 25%.

16 Claims, No Drawings

(56) References Cited

U.S. PATENT DOCUMENTS

| | | | |
|---|---|---|---|
| 5,369,196 A | 11/1994 | Matsumoto et al. | |
| 5,382,739 A | 1/1995 | Atkins et al. | |
| 5,462,995 A | 10/1995 | Hosaka et al. | |
| 5,498,815 A * | 3/1996 | Schaerfl et al. | 585/512 |
| 5,552,504 A | 9/1996 | Bennett et al. | |
| 5,637,400 A | 6/1997 | Brekner et al. | |
| 5,679,812 A | 10/1997 | Winter et al. | |
| 5,688,887 A | 11/1997 | Bagheri et al. | |
| 5,690,832 A | 11/1997 | Tavlarides et al. | |
| 5,731,254 A | 3/1998 | Winter et al. | |
| 5,811,379 A | 9/1998 | Rossi et al. | |
| 5,846,896 A | 12/1998 | Ewen | |
| 5,852,143 A | 12/1998 | Sishta et al. | |
| 5,859,159 A | 1/1999 | Rossi et al. | |
| 6,043,401 A | 3/2000 | Bagheri et al. | |
| 6,087,307 A | 7/2000 | Kaminski et al. | |
| 6,133,209 A | 10/2000 | Rath et al. | |
| 6,147,271 A | 11/2000 | Strebel et al. | |
| 6,180,575 B1 | 1/2001 | Nipe | |
| 6,388,032 B1 | 5/2002 | Yamaura et al. | |
| 6,414,090 B2 | 7/2002 | Minami et al. | |
| 6,414,091 B2 | 7/2002 | Moritomi et al. | |
| 6,479,722 B1 | 11/2002 | De Wet et al. | |
| 6,548,723 B2 * | 4/2003 | Bagheri et al. | 585/517 |
| 6,548,724 B2 * | 4/2003 | Bagheri et al. | 585/517 |
| 6,642,169 B2 | 11/2003 | Weatherhead | |
| 6,646,174 B2 | 11/2003 | Clarembeau | |
| 6,706,828 B2 | 3/2004 | DiMaio | |
| 6,713,438 B1 | 3/2004 | Baillargeon et al. | |
| 6,824,671 B2 | 11/2004 | Goze et al. | |
| 6,858,767 B1 | 2/2005 | DiMaio et al. | |
| 6,960,700 B1 | 11/2005 | Sethna et al. | |
| 7,053,157 B2 * | 5/2006 | Sita et al. | 526/86 |
| 7,060,768 B2 | 6/2006 | Brookhart et al. | |
| 7,129,197 B2 * | 10/2006 | Song et al. | 508/591 |
| 7,473,815 B2 | 1/2009 | Lambert et al. | |
| 7,544,850 B2 | 6/2009 | Goze et al. | |
| 7,547,811 B2 | 6/2009 | Kramer et al. | |
| 7,592,497 B2 | 9/2009 | Yang et al. | |
| 7,601,256 B2 | 10/2009 | Beall | |
| 2001/0041817 A1 | 11/2001 | Bagheri et al. | |
| 2001/0041818 A1 | 11/2001 | Bagheri et al. | |
| 2003/0055184 A1 | 3/2003 | Song et al. | |
| 2004/0022508 A1 | 2/2004 | Belardi et al. | |
| 2004/0033908 A1 | 2/2004 | Deckman et al. | |
| 2004/0087746 A1 | 5/2004 | Razavi | |
| 2004/0097772 A1 | 5/2004 | Deckers et al. | |
| 2004/0147693 A1 | 7/2004 | DiMaio | |
| 2004/0220359 A1 | 11/2004 | Abhari et al. | |
| 2004/0230016 A1 | 11/2004 | Blackbrow et al. | |
| 2005/0059563 A1 | 3/2005 | Sullivan et al. | |
| 2005/0101761 A1 | 5/2005 | Lambert et al. | |
| 2005/0183988 A1 | 8/2005 | Freerks et al. | |
| 2007/0000807 A1 | 1/2007 | Wu et al. | |
| 2007/0011832 A1 | 1/2007 | Keidel et al. | |
| 2007/0043248 A1 | 2/2007 | Wu et al. | |
| 2007/0208151 A1 | 9/2007 | Okada et al. | |
| 2009/0005279 A1 | 1/2009 | Wu et al. | |
| 2009/0281360 A1 | 11/2009 | Knowles et al. | |
| 2010/0069687 A1 | 3/2010 | Kosover et al. | |

FOREIGN PATENT DOCUMENTS

| | | |
|---|---|---|
| EP | 0 284 708 | 10/1988 |
| EP | 0 321 852 | 6/1989 |
| EP | 0 403 866 | 12/1990 |
| EP | 377306 | 8/1992 |
| EP | 0 513 380 | 11/1992 |
| EP | 0 613 873 | 9/1994 |
| EP | 349276 | 3/1995 |
| EP | 0 680 942 | 11/1995 |
| EP | 0 930 320 | 7/1999 |
| EP | 0 992 517 | 4/2000 |
| EP | 1 028 128 | 8/2000 |
| EP | 1 309 633 | 5/2003 |
| EP | 1 342 707 | 9/2003 |
| EP | 1 607 415 | 12/2005 |
| EP | 1 880 986 | 1/2008 |
| GB | 938069 | 9/1963 |
| IN | 191553 | 12/2003 |
| JP | 6336590 | 5/1993 |
| JP | 2005-200446 | 7/2005 |
| WO | 96/23751 | 8/1996 |
| WO | 99/67347 | 12/1999 |
| WO | 00/58423 | 10/2000 |
| WO | 02/14384 | 2/2002 |
| WO | 03/009136 | 1/2003 |
| WO | 03/051943 | 6/2003 |
| WO | 03/071369 | 8/2003 |
| WO | 03/104292 | 12/2003 |
| WO | 2004/046214 | 6/2004 |
| WO | WO 2007/011459 | 1/2007 |
| WO | WO 2007/011462 | 1/2007 |
| WO | WO 2007/011832 | 1/2007 |
| WO | WO 2007/011973 | 1/2007 |
| WO | WO 2007/011973 A1 | 1/2007 |
| WO | 2007/145924 | 12/2007 |
| WO | 2007/146081 | 12/2007 |
| WO | 2008/010862 | 1/2008 |
| WO | 2008/010865 | 1/2008 |
| WO | 2009/017953 | 2/2009 |
| WO | 2009/137264 | 11/2009 |

OTHER PUBLICATIONS

J. A. Brennen, "Wide-Temperature Range Synthetic Hydrocarbon Fluids", Ind. Eng. Chem. Prod. Res. Dev., 19, pp. 2-6 (1980).

K. Denbigh, "*The Kinetics of Continuous Reaction Processes: Application to Polymerization*", J. Applied Chem, 1951, vol. 1, p. 227-236.

K. Denbigh, "*Continuous Reactions: Part II. The Kinetics of Steady State Polymerisation*", Trans Faraday Soc., 1947, vol. 43, pp. 648-660.

A. Munoz-Escalona, "*Single-Site Supported Catalysts for Ethylene Polymerization*", Metallocene Tech., 1999, pp. 2242-2246.

Z. Fan et al., "*Effect of Ethoxy- and Methoxysilane Donors in Propene/1-Hexene Copolymerization With High-Yield Supported Ziegler-Natta Catalysts*", Macromolecular Chemistry and Physics, 1994, vol. 195, pp. 3889-3899.

G. Gokel ed, Dean's Handbook of Organic Chemistry, 2nd Edition, McGraw-Hill, 2004, available on-line at hhtp://knovel.com.

M. LeVan eet al., "*Adsorption and Ion Exchange*" Perry's Chemical Engineer's Handbook, 7th ed. 1997, pp. 16-1-16-66.

O. Levenspiel, "*Ch. 7 Design for Multiple Reactions*", Chemical Reaction Engineering, 2nd ed. 1972, pp. 196-209.

N. Naga et al., "*Effect of Co-Catalyst System on aA-Olefin Polymerization With Rac- and Meso-[Dimethylsilylenebis(2,3,5-Trimethyl-Cyclopentadienyl)]Zirconium Dichloride*", Macromol. Rapid Commun., 1997, vol. 18, pp. 581-589.

N. Naga et al, "*Polymerization Behavior of a-Olefins With Rac- and Meso-Type Ansa-Metallocene Catalysts: Effects of Cocatalyst and Metallocene Ligand*", Macromolecular Chemistry Physics, 1999, vol. 200, pp. 1587-1594.

F. Rodriguez, "*The Molecular Weight of Polymers*", Principles of Polymer Systems, 1970, Chapter 6, pp. 115-144.

M. Sacchi et al., "*Use of Different Alkoxysilanes As External Donors in $MgCl_2$ Supported Ziegler-Natta Catalysts to Obtain Propene/1-Butene Copolymers With Different Microstructure*", Macromolecular Chemistry and Physics, 1994, vol. 195, pp. 2805-2816.

T. Seraidaris et al., "*High-Molar-Mass Polypropene with Tunable Elastic Properties by Hafnocene/Borate Catalysts*", Journal of Polymer Science: Part A: Polymer Chemistry, 2006, vol. 44, pp. 4743-4751.

J. Wills, "*Synthetic Lubricants*", Lubrication Fundamentals, Marcel Dekker Inc., New York, 1980, pp. 75-80.

"*Mobil Releases SuperSyn PAOs*", Lubrication Engineers, 1999, vol. 55, Part 8, pp. 45.

TIBA data, "*TIBA datasheet*" available on-line at www.albermarle.com on Aug. 26, 2010.

\* cited by examiner

PROCESS FOR SYNTHETIC LUBRICANT PRODUCTION

CROSS-REFERENCE TO RELATED APPLICATIONS

This application claims priority to U.S. Provisional Application Ser. No. 61/069,826 filed Mar. 18, 2008, herein incorporated by reference in its entirety.

FIELD

The present disclosure relates to an improved process for the production of poly-alpha-olefins (PAOs) useful as synthetic lubricant basestocks.

BACKGROUND

The PAOs have been recognized for over 30 years as a class of materials which are exceptionally useful as high performance synthetic lubricant base stocks. They possess good flow properties at low temperatures, relatively high thermal and oxidative stability, low evaporation losses at high temperatures, high viscosity index, good friction behavior, good hydrolytic stability, and good erosion resistance. PAOs are not toxic and are miscible with mineral oils, other synthetic hydrocarbon liquids, fluids and esters. Consequently, PAOs are suitable for use in engine oils, compressor oils, hydraulic oils, gear oils, greases and functional fluids. The term PAO has become widely and conventionally employed as the name for these lubricant basestocks although the initial olefin oligomer is hydrogenated prior to use as a basestock in order to remove residual unsaturation and improve thermal and oxidative stability of the lube product. The use of PAOs as high quality lubricant basestocks is included as the subject of numerous textbooks, such as *Lubrication Fundamentals*, J. G. Wills, Marcel Dekker Inc., (New York, 1980), and *Synthetic Lubricants and High-Performance Functional Fluids*, 2nd Ed., Rudnick and Shubkin, Marcel Dekker Inc., (New York, 1999).

PAOs may be produced by the use of Friedel-Craft catalysts such as aluminum trichloride or boron trifluoride with boron trifluoride being the catalyst of choice. Boron trifluoride is preferably combined with a protic promoter, typically an alcohol such as isopropanol or butanol, water, or an acid, ester or an ether, to form a catalyst complex which may be used to promote oligomerization into products with the desired molecular weight highly branched oligomeric structure required for a combination of low pour point and high viscosity index in the lubricant products. The alpha olefins which are generally used are those in the $C_8$ to $C_{14}$ range, preferably 1-octene, 1-decene and 1-dodecene; the use of odd carbon number olefins has been found to be unfavorable. Olefins of this type may typically be formed by cracking or by the ethylene chain growth process. The boron trifluoride catalyst normally used in the oligomerization represents a significant cost in process schemes for producing polyalphaolefins since it is generally not recovered but, instead, inactivated by a water wash. The used, inactivated catalyst is often disposed of by deep-well injection in commercial operations producing polyalphaolefins, a disposal method which has some environmental considerations although various methods for recovering the boron trifluoride have been proposed.

In current low viscosity PAO process using the Friedel-Craft catalysts, the dimer or light fractions are recycled into the linear alpha-olefin feed to produce more lube base stock. These dimer or light fractions comprising mostly $C_8H_{16}$ to $C_{30}H_{60}$ oligomers (average $C_{20}H_{40}$), exhibit a relatively low average molecular weight of 280 or less, and are not very desirable as feed stock for the process because the isomerization which accompanies the oligomerization process, although valuable in terms of producing branched-chain higher oligomers which are excellent lubricants with high viscosity index and low pour point, also results in the dimer or light fraction composed of the lower oligomers which are themselves highly branched, highly substituted products with an unsaturated double bond in the middle of the molecule; they may be generally characterized as oligomers in the stated molecular weight range with significant short chain branching and highly substituted double bonds (tri- and tetra-substituted olefins). Being sterically hindered, the double bonds in these light co-products are less accessible and therefore less amenable to further reaction. Thus, these dimer or light fractions are less reactive toward further oligomerization. Furthermore, they are more highly branched olefins and the lube products from these branched molecules have less desirable VI, volatility and thermal/oxidative stability as a consequence of their structure. Removal of the dimer fraction prior to the final hydrogenation step, as described in U.S. Pat. No. 3,149,178, has therefore become routine practice.

The demand for high quality PAO, especially low viscosity/high VI/low pour point PAO is increasing fast and alternatives to the current Friedel-Craft process are being proposed. Supported, reduced chromium catalysts and metallocene catalyst systems have been proposed for such processes. A process using a metallocene catalyst for the production of 4 to 10 cSt, low viscosity PAO base stocks is described in WO 2007/011973 (Wu et al.). This technology is attractive because the metallocene-based low viscosity PAO has excellent lube properties. One disadvantage of this process so far, has been that when producing 4-10 cS PAO, some amount of dimer or light oligomers, smaller than $C_{30}$ are obtained as co-products. These light olefins cannot be used as lubricant base stocks as they are too volatile and they cannot be recycled into the metallocene-catalyzed process because they are usually more linear and with high degree of vinylidene or vinyl contents. The light fractions from the metallocene oligomerization process therefore represent a lube yield loss if they cannot be converted into lube products by other methods.

Co-pending U.S. Provisional Patent Application Ser. No. 61/008,095, filed 18 Dec. 2007, describes a process for producing high quality lube boiling range products from the low molecular weight alpha-olefin oligomers produced in the metallocene-catalyzed oligomerization process. The linear character of the light olefin by-products from the metallocene oligomerization step makes them a good choice for use as a feed for an oligomerization process using ionic liquid catalysts described in U.S. Ser. No. 61/008,095. The metallocene olefins, mainly dimers, can be oligomerized or co-oligomerized more readily than the branched olefins resulting from the Lewis acid catalyzed process and they produce lube base stocks with less chain branching and consequently better lube properties.

SUMMARY

The non-lube boiling range light olefinic fractions from the metallocene oligomerization process can be converted into high quality lube base stocks using Lewis acid catalysts. In this way, the total lube yields from the metallocene-catalyzed, low viscosity PAO oligomerization process may be significantly increased with a consequent improvement in process economics. The linear character of the light olefin by-products from the metallocene oligomerization makes them a good choice for use as a feed for the Lewis acid catalyzed oligomerization step as they can be oligomerized or co-oligomerized more readily than the branched olefins and produce lube base stocks with less chain branching and consequently better lube properties.

According to the present disclosure, therefore, a process for the preparation of oligomeric poly alpha-olefins comprises oligomerizing a low molecular weight olefin feed in the presence of a Lewis acid catalyst under oligomerization conditions. The low molecular weight olefins used as a feed or feed component of the present process comprise the light olefinic by-product fraction including the dimers and light fractions from the metallocene-catalyzed PAO oligomerization process; these olefin feeds may be characterized as having a molecular weight in the range of 120 to 600 and a terminal olefin content of at least 25%.

The catalyst used in the present oligomerization step comprises a Lewis acid such as boron trifluoride or aluminum trichloride. In general the amount of the Lewis acid catalyst is typically between 0.1 to 10 wt % and in most cases between 0.2 to 3 or 5 wt % based on total amount of olefin feed material.

There are several advantages to using the low molecular weight alpha-olefin oligomers from the metallocene process for oligomerization or co-oligomerization: (1) flexibility and economy in utilizing a new, previously wasted feedstock, which can be comprised of specific carbon number fractions, a mixture of selected fractions or, most desirably, use of the total, unfractionated PAO distillate byproduct, with or without removal of α-olefins; (2) the greater reactivity afforded by the presence of the terminal vinylidene double bond results in a liquid product with highly desirable properties and high performance features.

DETAILED DESCRIPTION

All numerical values within the detailed description and the claims herein are modified by "about" or "approximately" the indicated value, and take into account experimental error and variations that would be expected by a person having ordinary skill in the art.

Olefin Feed

The olefin feed used in the present process comprises a light olefinic by-product fraction including the dimers and light fractions from the metallocene-catalyzed PAO oligomerization process. These intermediate light fractions may be generally characterized as the $C_{42}$- (usually $C_{40}$-) olefinic distillate fractions comprising a mixture of highly reactive oligomers derived from the original alpha-olefin starting material; the fractions contain mostly $C_8H_{16}$ to $C_{30}H_{60}$ oligomers (average $C_{20}H_{40}$) which exhibit a molecular weight in the range of 120 to 600, typically from 140 to 560 (an average of 200) and contain a terminal olefin content of at least 25% of total olefinic unsaturation. The vinylidene content of the mixture may, in fact, be at least 50%, for example, 60 or even 80%, depending on the metallocene catalyst and the oligomerization conditions. The high amount of vinylidene olefin with correspondingly less of other types of olefinic unsaturation in the alpha-olefin dimer/trimer fraction is unique, as confirmed by 1H and 13C-NMR and lends a distinction to the present process which utilizes these unique olefins as the starting material for a subsequent oligomerization with a Lewis acid catalyst to produce lube range product with advantageous properties.

The metallocene-derived intermediate used as the feed is produced by the oligomerization of an alpha-olefin feed using a metallocene oligomerization catalyst. The alpha olefin feeds used in this initial oligomerization step are typically alpha-olefin monomers of 4 to 24 carbon atoms, usually 6 to 20 and preferably 8 to 14 carbon atoms, such as 1-butene, 1-hexene, 1-octene, 1-decene, 1-dodecene, and 1-tetradecene. The olefins with even carbon numbers are preferred as are the linear alpha-olefins although it is possible to use branched-chain olefins containing an alkyl substituent at least two carbons away from the terminal double bond. These 1-olefins may be co-oligomerized with other monomers in the same molecular weight range. These starting materials are oligomerized using a metallocene catalyst to produce a range of products extending from the low molecular weight dimers and trimers which form the majority of the feed for the present Lewis acid catalyzed step as well as higher molecular weight oligomers in the lube boiling range which are directly useful as lube base stocks. The initial feed olefins are preferably treated to remove catalyst poisons, such as peroxides, oxygen, sulfur, nitrogen-containing organic compounds, and or acetylenic compound as described in WO 2007/011973. This treatment is believed to increase catalyst productivity, typically more than 5 fold, and in favorable cases, more than 10 fold. The lowest molecular weight oligomers from these alpha-olefin starting materials typically have carbon numbers ranging from $C_8$ to $C_{30}$, in most cases from $C_{16}$ to $C_{30}$. These small oligomers are usually separated by fractionation from the higher oligomers with carbon number of greater than $C_{30}$, for example $C_{40}$ and higher which are typically used as the high performance lube base stocks.

The initial oligomerization step using the metallocene catalyst is carried out under the conditions appropriate to the selected alpha-olefin feed and metallocene catalyst. A preferred metallocene-catalyzed alpha-olefin oligomerization process is described in WO 2007/011973, to which reference is made for details of feeds, metallocene catalysts, process conditions and characterizations of products. The light olefinic oligomers produced from that process and which are used as feed in the present oligomerization step may suitably be separated from the raw mixture of alpha-olefin oligomers obtained from the metallocene oligomerization step by distillation with the cut point set at a value dependent upon the fraction to be used as lube base stock or the fraction to be used as feed for the Lewis acid catalyzed process step. As noted in WO 2007/011973, the PAO oligomers selected for the lube base stock fraction are liquids which have no melting point above 0° C., a pour point less than 0° C., typically less than −45° C. or even lower, e.g. less than −75° C., preferably with a $KV_{100}$ of 1.5-20 cSt which in most cases will be selected depending on desired product specifications as in the range from 1.5 to 10 cSt. The volatility of the lube range fraction as measured by the Noack Volatility test (ASTM D5800) is typically of 25 wt % or less, preferably 14 wt % or less. The Bromine number of the lube fraction is typically of 1.8 or more, to be reduced by hydrogenation prior to use as a lube base stock. In terms of molecular weight range, the fraction selected for use as lube base stock typically has a selectivity of 80% or more for $C_{20}$ and greater hydrocarbons, preferably 85% or more, preferably 90% or more, more preferably 95% or more, preferably 98% or more, preferably 99% or more for $C_{20}$ and greater hydrocarbons. The corresponding selectivities for $C_{20}$ and lower hydrocarbons are normally 50% or less, preferably 40% or less, e.g. 20% or less, 10% or less.

The metallocene catalysts used in the process of WO 2007/011973 are unbridged, substituted bis-cyclopentadienyl transition metal compounds. One preferred class of catalysts are the highly substituted metallocenes that give high catalyst productivity and with low product viscosity. Another preferred class of metallocenes are unbridged and substituted cyclopentadienes, including unbridged and substituted or unsubstituted indenes and or flourenes. Optionally an activator for the metallocene component may be used at a molar ratio of transition metal compound to activator typically from 10:1 to 0.1:1 e.g. a methylaluminoxane (MAO); if an organoaluminum compound, e.g. an alkyl aluminum compound, is used as the activator, the molar ratio of alkyl aluminum compound to transition metal compound may be in the range of 1:4 to 4000:1. Oligomerization conditions typically call for hydrogen to be present at a partial pressure of 345 kPa (50 psi) or less, based upon the total pressure of the reactor, typically between 7 kPa (1 psi) and 345 kPa (50 psi), (preferably between 20 kPa (3 psi) and 275 kPa (40 psi), e.g. between 35 kPa (5 psi) and 210 kPa psi (30), or 175 kPa (25 psi) or less, preferably 70 kPa (10 psi) or less. Hydrogen is normally present at a concentration of 10 to 10,000 ppm by weight, preferably 25 to 7,500 ppm, e.g. 25 to 5,000 ppm with the alpha-olefin monomer(s) feed at 10 volume percent or more based upon the total volume of the catalyst/activator/co-activator solutions, monomers, and any diluents or solvents present in the reaction. Residence time of the reaction is typically at least 5 minutes, and the temperature in the reaction zone is controlled not to be more than 10° C. during the reaction. The metallocene catalyst components, activators and typical and preferred reaction conditions and product parameters are all described in WO 2007/011973, to which reference is made for such description.

An alternative metallocene-catalyzed alpha-olefin oligomerization process which may yield dimer fractions useful as feed for the second oligomerization step of the present disclosure is described in U.S. Pat. No. 6,548,724 and additional metallocene-catalyzed oligomerization processes in the references cited in this patent, to which reference is made for details of such alternative processes. Other metallocene polymerization processes which may yield dimer fractions useful as feed for the second oligomerization step of the present disclosure are described in WO2007011459, WO2007011462, and in U.S. Pat. Nos. 5,017,299 and 5,186,851, to which reference is also made for information concerning such metallocene-catalyzed oligomerization processes. Light olefin PAO oligomer fractions from such metallocene oligomerization processes using alpha-olefin starting materials may be used as the feeds in the present process which utilizes such light olefinic by-products as a component of the feed.

The dimers used as feed for the present process possess at least one carbon-carbon unsaturated double bond. The unsaturation is normally more or less centrally located at the junction of the two monomer units making up the dimer as a result of the non-isomerizing polymerization mechanism characteristic of metallocene processes. If the initial metallocene polymerization step uses a single 1-olefin feed to make an alpha-olefin homopolymer, the unsaturation will be centrally located but if two 1-olefin comonomers have been used to form a metallocene copolymer, the location of the double bond may be shifted off center in accordance with the chain lengths of the two comonomers used. In any event, this double bond is vinylic or vinylidenic in character. The terminal vinylidene group is represented by the formula RaRbC=CH$_2$, referred to as vinyl when Rb=H. The amount of unsaturation can be quantitatively measured by bromine number measurement according to ASTM D1159 or equivalent method, or according to proton or carbon-13 NMR. Proton NMR spectroscopic analysis can also differentiate and quantify the types of olefinic unsaturation.

The characteristic vinylidene compounds which make up at least 25% of the olefin feed for the present oligomerization process may therefore be defined as unsaturated hydrocarbons of the formula:

where $R^1$ and $R^2$, which may be the same or different, together have from 6 to 40 carbon atoms and $R^1$ is a hydrocarbon group of 1 to 24 carbon atoms, $R^2$ is $R^1$ or H. Typically, $R^1$ and $R^2$ together have from 16 to 30 carbon atoms, preferably 8 to 11 carbon atoms and in the case of dimers prepared from single monomers, $R^1$ and $R^2$ are the same. In the preferred dimers, $R^1$ and $R^2$ each have from 7 to 13 carbon atoms.

The light olefin (mostly dimer and trimer) fraction from the metallocene oligomerization process may be used as the sole feed material in the present process or it may be used as one of the olefinic feed components together with an alpha-olefin of the type used as the olefin starting material for the metallocene oligomerization step. Alpha-olefins or other internal olefins with linear or branched structures, or mixtures of them may be used together with the low molecular weight alpha-olefin oligomers as feeds. The metallocene light olefinic alpha-olefin oligomer may therefore be used as feed combined, for example, with a monomeric alpha-olefin of 6 to 24 carbon atoms, usually 6 to 20 and preferably 8 to 14 carbon atoms, preferably olefins with an carbon numbered olefin (such as 1-decene, 1-octene, 1-dodecene, 1-hexene, 1-tetradecene, 1-octadecene or mixtures thereof). The linear alpha-olefins are preferred if optimal lube properties are to be achieved but it is possible also to use branched-chain olefins containing an alkyl substituent at least two carbons away from the terminal double bond. The proportion in which the light alpha-olefin oligomer may be used is likely to be set in practical operation by the availability of starting materials and the parameters which are desired for the products which themselves are also dependent on the reaction conditions used in the Lewis acid catalyzed oligomerization step of the present process. Typical ratios are from 90:10 to 10:70 or 10:90 and more usually 80:20 to 20:80 by weight but normally the light alpha-olefin oligomer (dimer/trimer) fraction will make up at least 50% by weight of the olefinic feed material since the properties of the final product, dependent in part upon the starting material, are favorably affected by increasing proportions of the light oligomer fraction. Preferred proportions for the light oligomer fraction in the olefin feed are therefore at least 50% and more preferably at least 60%, 70%, or 80% by weight.

Lewis Acid Catalyzed Oligomerization

The oligomerization of the light olefin fraction is carried out in the presence of a catalyst comprising a Lewis acid. The Lewis acid catalysts which may be used for olefin oligomerization reactions include the metal and metalloid halides conventionally used as Friedel-Crafts catalysts, suitable examples of which include AlCl$_3$, BF$_3$, AlBr$_3$, TiCl$_3$, and TiCl$_4$ either as such or with a protic promoter. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g. WOx/ZrO$_2$, WOx/MoO$_3$) may also be used although these are not generally as favored economically as the metal and metalloid halides which are used in the conventional PAO oligomerization process. In general, between 0.1 to 10 wt % and preferably between 0.2 to 3 or 5 wt % based on total feed, of the acid catalyst is used in the oligomerization or co-oligomerization process.

The Lewis acid catalysts which will be most frequently used for the oligomerization of the light olefin fraction from the metallocene oligomerization are the metal and metalloid halide catalysts which are typically used in the conventional PAO oligomerization process, for the most part, aluminum trichloride and boron trifluoride, of which the latter is preferred. Boron trifluoride, however, is not particularly suitable for use as a catalyst in the oligomerization unless it is used in combination with a protic promoter. Various promoters of this type are well established for the $BF_3$-catalyzed olefin oligomerization process and include materials such as water, alcohols such as the lower ($C_1$-$C_6$) alkanols including ethanol, isopropanol or butanol, acids which may be an organic acid e.g. a carboxylic acid or its anhydride such as acetic acid, propionic acid, or butanoic acid or acetic anhydride, or an inorganic acid such as phosphoric acid as described in U.S. Pat. No. 3,149,178, an ester such as ethyl acetate, as described in U.S. Pat. No. 6,824,671, an alcohol alkoxylate such as a glycol ether, e.g. ethylene glycol monomethyl ether (2-methoxyethanol) or propylene glycol monoethyl ether or an ethoxylate derived from mixed $C_2$ to $C_{24}$, preferably $C_2$ to $C_{18}$ and most preferably $C_6$ to $C_{12}$ straight chain alcohols, as described in U.S. Pat. No. 5,068,487 and ethers such as dimethyl ether, diethyl ether or methyl ethyl ether, ketones, aldehydes and alkyl halides. The protic promoter forms a catalyst complex with the boron trifluoride and it is the complex which serves as a catalyst for the oligomerization; this complex usually contains an excess of boron trifluoride which is adsorbed in the mixture.

The low molecular weight alpha-olefin oligomer from the metallocene oligomerization step which is oligomerized in the presence of the Lewis acid catalyst typically has a number average molecular weight in the range of 120 to 600 with a terminal olefin content greater than 25%. It is generally preferable to have a higher amount of terminal olefins in the feed.

It is possible to use solvents or diluents in the Lewis acid catalyzed oligomerization step but if the catalyst system being used is a liquid, this may also function as the solvent or diluent for the reaction so that no additional solvent or diluent is required Additional liquids which are non-reactive to the selected catalyst system may, however, be present if desired, for example, to control viscosity of the reaction mixture or to carry off heat of reaction by evaporation with reflux of the condensed vapor. Hydrocarbons such as alkanes and aromatics e.g. hexane or toluene, are suitable for this purpose. Thus, the light alpha-olefin oligomer reactant, either as such or with additional alpha-olefin co-feed may be oligomerized directly in the presence of the catalyst system with or without the addition of solvent or diluent. The reaction will normally be carried out in a closed environment when gaseous catalysts such as boron trifluoride are used, usually under inert atmosphere, e.g. nitrogen.

The temperature of the Lewis acid-catalyzed oligomerization reaction can usefully vary in practical operation between −10° C. to 300° C., preferably between 0° C. to 75° C. The system may operate under atmospheric pressure since the system typically exhibits low vapor pressures at the temperatures normally used for this process. It may, however, be operated under mild pressure if it is desired to maintain a closed reaction environment, e.g. under autogenous pressure. When using a solid Lewis acid as the catalyst, the oligomerization will normally be carried out using a fixed bed of the catalyst in a downflow mode although alternative forms of operation, e.g. in a stirred tank reactor are possible.

Following completion of the oligomerization reaction, the catalyst activity may be quenched by addition of water or a dilute aqueous base such as 5 wt % NaOH solution. The organic layer may be separated and distilled to remove components other than the base stock. When promoted $BF_3$ catalyst is used, the gaseous $BF_3$ and promoter may be recycled if not deactivated at the end of the reaction. When a solid catalyst is used, a simple filtration is all that is needed to separate the catalyst from the oligomer product if the reaction has not been carried out in a fixed bed. The oligomer product may then be fractionated to remove any unreacted light olefin and the oligomer in the desired boiling range sent for hydrogenation to remove residual unsaturation.

Oligomer Product

The formation of the oligomer product from the metallocene oligomer intermediate may be represented by the following scheme:

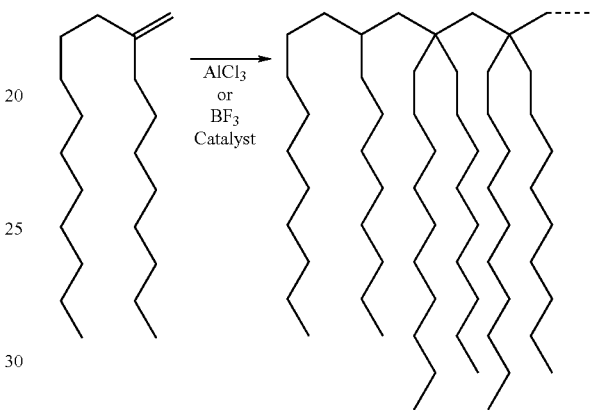

In this case, the portion of the final oligomer product shown is a trimer of the PAO reactant with a highly branched chain structure which may be expected to constitute a lube base stock component of low volatility, low pour point and high viscosity index. Depending on the carbon number of the starting material and the reaction conditions selected, however, the product may be a dimer, trimer or a higher oligomer with successive units attached through the double bond sites of the reactant. The degree of chain branching will largely be determined by the reactant so that if the metallocene-produced PAO intermediate itself has some degree of chain branching (as by the use of a branched chain olefin as feed to the metallocene oligomerization system) additional branching will be present in the final product from the Lewis acid catalyzed reaction. However, as pointed out above, the metallocene oligomers are largely linear oligomers with a central olefinic double bond at which addition takes place.

The oligomer products from the Lewis acid catalyzed oligomerization step are notable for their combination of rheological properties, possessing both low pour point and high viscosity index. Pour points are generally below −40° C. even in the case of the higher molecular weight oligomers with viscosities (100° C.) of 20 or higher. Pour points (ASTM D97 or equivalent) generally range between −40 and −55° C., usually below −45° C. Viscosity indices (ASTM D2270) are generally above 130 and usually are in the range of 135 to 150. Product viscosity may be varied by variation of the oligomerization conditions, particularly, reaction temperature and reaction time with higher temperatures and durations resulting in higher molecular weight/higher viscosity products. The lubricant ($C_{30}$+) fraction of the product will typically be a 4-300 cSt (100° C.) material but extra-low viscosity products 2-4 cSt (100° C.) may also be obtained for use in lubricants in which a low viscosity basestock is required.

Products in the economically important 4-6 cSt (100° C.) range are readily achievable, making it possible to improve the overall lubricant yield (based on alpha-olefin starting material) by this use of the dime/trimer by-product fraction from the metallocene oligomerization which previously could not be included in the lubricant fraction. In most cases, the demand for low viscosity, high quality lubricants will tend towards a range of 4-40, e.g. 4-30 or 6-40 cSt (100° C.) basestocks and these are readily achievable as products of the present oligomerization process. The molecular weights of the product typically range from 420 upwards, in most cases upwards of 600 and extending typically up to 2,000 for oligomers with viscosities in the range of 25-30 cSt (100° C.). Higher molecular weights and corresponding viscosities may be achieved by suitable choice of reaction conditions. Values of the polydispersity index (PDI) are typically from 1.15 to 1.4 with the higher values in this range being associated with the higher molecular weight oligomers in which the number of different oligomer species has increased with the increasing degree of oligomerization. Relatively high levels of product conversion (dimer to oligomer) in the oligomerization are readily achievable in the range typically over 90 weight percent. The lubricant fraction ($C_{30}+$) is normally 85 weight percent of the product or higher, typically 90 weight percent.

The overall reaction scheme enabled by the present oligomerization process may be represented as follows, starting from the original alpha-olefin feed passing through the metallocene dimer/trimer intermediate product used as the feed for the present oligomerization step:

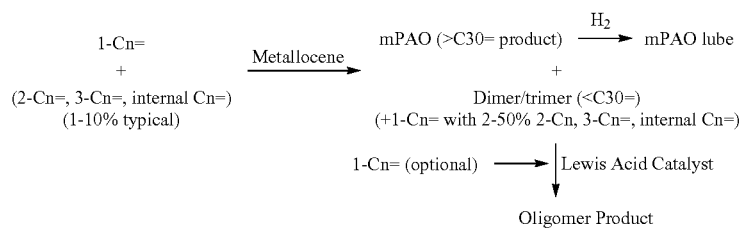

The lube range oligomer product from the Lewis acid catalyzed step is desirably hydrogenated prior to use as a lubricant basestock in order to remove any residual unsaturation and so as to stabilize the product. The hydrogenation may be carried out in the manner conventional to the hydrotreating of conventional PAOs, using, for example, a metal (usually a noble metal) hydrogenation catalyst.

In the Examples below, the metallocene dimer fraction may be produced using a synthesis method of the type described in WO2007011973, WO2007011832 or WO 2007011459. In the preparative procedures actually used, toluene solvent and feed alpha-olefins were purified according to the methods described in these publications and all synthesis steps and manipulations were carried out under nitrogen atmosphere to avoid any catalyst deactivation or poison by air, oxygen, moisture and other poisons.

EXAMPLES

Metallocene PAO can be synthesized using a batch mode of operation using the following exemplary procedure. Purified 1-decene (50 gram) and 3.173 gram of triisobutylaluminum (TIBA) stock solution are charged into a 500 ml flask under nitrogen atmosphere. The reaction flask is then heated to 120° C. with stirring. A solution in an additional funnel mounted on the reaction flask containing 20 gram toluene, 0.079 gram TIBA stock solution, 0.430 gram stock solution of rac-ethyl-enebis(4,5,6,7-tetrahydro-1-indenyl)zirconium dichloride and 0.8012 NCA stock solution was added to the 1-decene mixture within 15 minutes while maintaining reaction temperature close to 120° C., no more than 3° C. higher or lower. The reaction mixture is stirred at reaction temperature for 16 hours. The heat is then turned off and the mixture quenched with 3 ml isopropanol. The crude product is then washed with 100 ml of a 5% aqueous NaOH solution, followed by 100 ml deionized water three times. The organic layer is then separated and dried with 20 gram sodium sulfate for one hour. The solid is filtered off and the filtrate distilled first by low vacuum distillation to remove toluene, unreacted 1-decene and the light olefin dimer fraction, followed by high vacuum distillation at 160° C./1 millitorr vacuum to isolate $C_{30}$ and higher oligomers. The dimer fraction may then be separated from the toluene and unreacted monomer by distillation.

Illustrative Example 1

Oligomerization of Light Polyalphaolefins Using $AlCl_3$ mPAO-dimer produced by the general procedure described above (50.4 g neat) was charged with 0.4 g water into a 500 ml round bottom flask under nitrogen atmosphere. Anhydrous $AlCl_3$ (2.5 g) was added very slowly to maintain the temperature 0-5° C. After addition, the reaction was stirred for 4 hours at 0-5° C. after which toluene (100 ml) was added. The reaction mixture was allowed to warm to room temperature and stirring was then continued for 16 hours. The reaction was stopped by adding 25 ml water. The product was washed with water (4×50 ml) and (1×50 ml) brine until the aqueous layer attained pH-7. The organic layer was dried and filtered. The low boiling (toluene) component was then removed by a rotary evaporator and the high boiling component (PAO-Dimer) separated by distillation using a Kugelrohr at 160-170° C. under vacuum. The final product was characterized by IR, GC, NMR and GPC. The GC analysis showing 6.7% PAO-Dimer, 93.3% of lube product. The distilled oligomer was found to display the properties as shown in Table-1.

TABLE 1

| | |
|---|---|
| KV 100° C. | 7.94 CSt |
| KV 40° C. | 57.09 CSt |
| Viscosity Index | 105 |
| Pour Point | −57° C. |

Illustrative Example 2

Co-Oligomerization of Polyalphaolefins with 1-Decene using $AlCl_3$

The same mPAO-Dimer (40 g neat) as used in Example 1 with 1-decene (20 g) and water (0.45 g) was charged into a 500 ml round bottom flask under nitrogen atmosphere. Anhydrous $AlCl_3$ (3 g) was added very slowly to maintain the temperature 0-5° C. After addition, the reaction mixture was stirred for 4 hours at 0-5° C. and 100 ml toluene was then added. The reaction mixture was allowed to warm to room temperature and stirring was then continued for 16 hours. The reaction was stopped by adding 50 ml water and 75 ml toluene. The product was washed with water (4×75 ml) and (1×750 ml) brine until the aqueous layer attained a pH of ~7. The organic layer was dried and filtered. The low boiling (toluene) component was removed by a rotary evaporator and the high boiling component (PAO-Dimer) by Kugelrohr at 160-170° C. under vacuum. The final oligomer product was analyzed by IR, GC, NMR and GPC. The GC analysis showing the product conversion 95%, 6.31% PAO-Dimer and 93.7% of lube product. The distilled oligomer was found to display the properties as shown in Table-2.

TABLE 2

| | |
|---|---|
| KV 100° C. | 13.46 CSt |
| KV 40° C. | 115.12 CSt |
| Viscosity Index | 114 |
| Pour Point | −51° C. |

Illustrative Examples 3-5

Co-Oligomerization of PAO-Dimer and 1-Decene Using $AlCl_3$

Anhydrous $AlCl_3$ (2.7 g) and 12.0 g decane were charged into a 500 ml round bottom flask under $N_2$ atmosphere. A mixture of 30.23 g of the same neat mPAO-dimer and 15.16 g 1-decene (Example 3) was added very slowly followed by 0.121 g of water with 5 g decane with vigorous stirring at below 40° C. The $AlCl_3$ catalyst concentration was equivalent to 2.5 wt %. After the addition of the water, the reaction mixture was stirred for 3 hours at 40° C. when the reaction was stopped by adding 50 ml water and 150 ml toluene. The product was washed with water (4×120 ml) and (1×100 ml) brine until the aqueous layer pH was ~7. The product was then filtered and dried. The low boiling (toluene) component removed by Rotovap™ and the high boiling component by air bath oven at 160-170° C. under vacuum. The final product was analyzed by GC, and GPC.

Examples 4 and 5 were carried out in the same way under the same conditions using different molar ratios of mPAO dimer to decene, as indicated in Table 3 below.

The molecular weight ratios (Mw, Mn), product conversion and lube yield of the distilled oligomers are shown in Table 3, and their rheological properties in Table 4.

Illustrative Example 6

Oligomerization of PAO-Dimer and 1-Decene Using $AlCl_3$

The procedure of Example 3 was repeated using the same reaction temperature, $AlCl_3$ catalyst and catalyst concentration but using only the mPAO dimer as the feed (no decene), with a reaction time of only 0.5 hour to produce a lower molecular weight/lower viscosity oligomer product.

The molecular weight ratios (Mw, Mn), product conversion and lube yield of the distilled oligomer are shown in Table 3 and rheological properties in Table 4 and demonstrate the potential for producing a low viscosity (4-6 cSt) product using the metallocene dimer as the starting material.

TABLE 3

| Ex. | Feed | Mn/Mw | Mw/Mn | Prod. Conv. (%)[1] | Lube Prod. (%)[2] |
|---|---|---|---|---|---|
| 3 | mPAO Dimer + 1-Decene (2:1) | 1326/1639 | 1.24 | 95 | 93 |
| 4 | mPAO Dimer + 1-Decene (1:1) | 1503/1961 | 1.3 | 88 | 89 |
| 5 | mPAO Dimer + 1-Decene (1:2) | 1764/2414 | 1.37 | 92 | 91 |
| 6 | PAO Dimer | 839/988 | 1.18 | 91 | 84 |

Notes:
[1]Product conversion: amount of or % of monomer or feed converted to the product.
[2]Lube Product: amount of product above C30+ determined by GC.

TABLE 4

| | Product Oligomer Rheology | | | |
|---|---|---|---|---|
| Ex. | KV, 40° C. | Kv 100° C. | VI | Pour Pt. ° C. |
| 3 | 119.80 | 15.42 | 135 | −48 |
| 4 | 172.34 | 20.33 | 138 | −45 |
| 5 | 269.1 | 27.9 | 137 | −42 |
| 6 | 27.1 | 5.46 | 141 | −48 |

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of this disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

What is claimed is:

1. A process to produce a poly alpha-olefin (PAO) comprising:
   a) contacting one or more $C_4$ to $C_{24}$ alpha olefin monomers with a metallocene compound, and optionally an activator to produce a low molecular weight PAO comprising a mixture of oligomers having a number average molecular weight in the range of 120 to 600 and containing a terminal olefin content of at least 25 wt % of total olefinic unsaturation, and
   b) subsequently contacting at least a portion of said low molecular weight PAO with a Lewis acid catalyst and optionally one or more $C_4$ to $C_{24}$ alpha olefin monomers to produce a liquid PAO, wherein said liquid PAO has a mass average molecular weight of at least 988.

2. A process according to claim 1 in which the low molecular weight PAO comprises a mixture of $C_8H_{16}$ to $C_{30}H_{60}$ oligomers.

3. A process according to claim 1 in which the terminal olefin content of the low molecular weight PAO is at least 50 wt % of total olefinic unsaturation.

4. A process according to claim 1 in which the Lewis acid catalyst comprises a Friedel-Craft catalyst.

5. A process according to claim 4 in which the Friedel-Craft catalyst comprises an aluminum halide or boron halide.

6. A process according to claim 4 in which the Lewis acid catalyst comprises an aluminum halide or boron halide and a protic promoter.

7. A process according to claim 6 in which the protic promoter is at least one compound selected from the group comprising water, lower alkanols, protic acids, and esters.

8. A process according to claim 1 in which the amount of the Lewis acid catalyst is between 0.2 to 5 wt % based on total amount of low molecular weight PAO oligomer feed.

9. A process according to claim 1 in which the oligomerization in the presence of the Lewis acid catalyst is carried out at a temperature from 0 to 75° C.

10. A process according to claim 1 in which the amount of the Lewis acid catalyst is between 0.2 to 5 wt % based on total amount of said portion of low molecular weight PAO and said optional one or more $C_4$ to $C_{24}$ alpha olefin monomers.

11. A process according to claim 1, wherein the low molecular weight PAO comprises at least 25 wt % of vinylidene compounds of the formula:

$$R^1R^2C{=}CH_2$$

where $R^1$ and $R^2$ together have from 6 to 40 carbon atoms and $R^1$ is a hydrocarbon group of 1 to 24 carbon atoms, and $R^2$ is a hydrocarbon group of 1 to 24 carbon atoms and may be the same as $R^1$.

12. A process according to claim 11 in which $R^1$ and $R^2$ together have from 16 to 30 carbon atoms.

13. A process according to claim 12 in which $R^1$ and $R^2$ each have 8 to 11 carbon atoms.

14. A process according to claim 11 in which the low molecular weight PAO comprises at least 50 wt % of the vinylidene compounds of the formula $R^1R^2C{=}CH_2$.

15. A process according to claim 14 in which the low molecular weight PAO comprises at least 60 wt % of the vinylidene compounds of the formula $R^1R^2C{=}CH_2$.

16. A process according to claim 1 wherein the liquid PAO has a kinematic viscosity at 100° C. of between 2-4 cSt or between 4-300 cSt.

* * * * *